(12) United States Patent
Li

(10) Patent No.: US 11,664,121 B2
(45) Date of Patent: *May 30, 2023

(54) MEDICAL DATA PROCESSING METHOD, CLUSTER PROCESSING SYSTEM AND METHOD THEREOF

(71) Applicant: BOE TECHNOLOGY GROUP CO., LTD., Beijing (CN)

(72) Inventor: Zhenglong Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 127 days.

This patent is subject to a terminal disclaimer.

(21) Appl. No.: 17/341,881

(22) Filed: Jun. 8, 2021

(65) Prior Publication Data

US 2021/0304884 A1 Sep. 30, 2021

Related U.S. Application Data

(63) Continuation of application No. 15/742,345, filed as application No. PCT/CN2017/085726 on May 24, 2017, now Pat. No. 11,062,803.

(30) Foreign Application Priority Data

Sep. 8, 2016 (CN) .......................... 201610810601.8

(51) Int. Cl.
*G16H 40/20* (2018.01)
*G16H 40/67* (2018.01)
*G16H 10/60* (2018.01)

(52) U.S. Cl.
CPC ............. *G16H 40/20* (2018.01); *G16H 10/60* (2018.01); *G16H 40/67* (2018.01)

(58) Field of Classification Search
CPC ......... G16H 10/60; G16H 40/20; G16H 40/67
(Continued)

(56) References Cited

U.S. PATENT DOCUMENTS

| 2004/0122703 A1* | 6/2004 | Walker ................... G16H 50/70 706/45 |
| 2005/0270973 A1 | 12/2005 | Raev et al. |
| 2014/0173091 A1* | 6/2014 | Lipstone ............ H04L 61/2503 709/224 |

FOREIGN PATENT DOCUMENTS

| CN | 101146334 A | 3/2008 |
| CN | 102567396 A | 7/2012 |

(Continued)

OTHER PUBLICATIONS

Obaidat, Mohammad Salameh; A 68000 Based Modular Multiprocessor System: Design and Simulationanalysis (Image-Processing, Multiple-Bus); The Ohio State University. ProQuest Dissertations Publishing, 1986. 8618826. (Year: 1986).*

(Continued)

*Primary Examiner* — Hiep V Nguyen
(74) *Attorney, Agent, or Firm* — Collard & Roe, P.C.

(57) ABSTRACT

A medical data cluster processing system, including: a cluster initiator device and cluster participant devices that have signal connection with each other. The cluster initiator device sends model data and medical data to at least two cluster participant devices; the cluster participant devices receive the model data and the medical data from the cluster initiator device, process the medical data based on the model data to obtain second processing data, and sends the second processing data to the cluster initiator device; and the cluster initiator device receives the second processing data sent from the at least two cluster participant devices, and comprehensively processes the second processing data to obtain a medical data processing result. A medical data processing (Continued)

300 receiving the model data and the medical data from the first electronic device, the second electronic device having signal connection with the first electronic device — S301 processing, by the at least two second electronic devices respectively, the medical data based on the model data to obtain the second processing data — S302 sending the second processing data to the first electronic device, so that the first electronic device comprehensively processes the second processing data received from the at least two second electronic devices to obtain a medical data processing result — S303 method and a medical data cluster processing method are also provided.

20 Claims, 3 Drawing Sheets

(58) Field of Classification Search
USPC .......................................................... 705/2
See application file for complete search history.

(56) References Cited

FOREIGN PATENT DOCUMENTS

| CN | 102866424 A | 1/2013 | | |
|---|---|---|---|---|
| CN | 104252570 A | 12/2014 | | |
| CN | 104392188 A | 3/2015 | | |
| CN | 104537682 A | 4/2015 | | |
| CN | 104730043 A | 6/2015 | | |
| EP | 2629247 A1 * | 8/2013 | ....... | G06F 17/30598 |

OTHER PUBLICATIONS

International Search Report of PCT/CN2017/085726 in Chinese, dated Aug. 30, 2017 with English translation.
Notice of Transmittal of the International Search Report of PCT/CN2017/085726 in Chinese, dated Aug. 30, 2017.
Written Opinion of the International Searching Authority of PCT/CN2017/085726 in Chinese, dated Aug. 30, 2017 with English translation.
Chinese Office Action in Chinese Application No. 201610810601.8, dated May 8, 2020 with English translation.

* cited by examiner

MEDICAL DATA PROCESSING METHOD, CLUSTER PROCESSING SYSTEM AND METHOD THEREOF

CROSS REFERENCE TO RELATED APPLICATIONS

This application is a continuation application of U.S. patent application Ser. No. 15/742,345 filed on Jan. 5, 2018 which is a National Stage of PCT/CN2017/085726 filed on May 24, 2017, which claims priority under 35 U.S.C. § 119 of Chinese Application No. 201610810601.8 filed on Sep. 8, 2016, the disclosures of which are incorporated by reference.

TECHNICAL FIELD

Embodiments of the present disclosure relate to a medical data processing method, a medical data cluster processing system, and a medical data cluster processing method.

BACKGROUND

Currently, processing of medical data mainly depends on some high-performance devices with specific purposes, such as a high-end device with high computing power. However, such a high-end device is not usually equipped in general hospitals. For grassroots medical clinics, or in some remote areas, a medical device with high computing performance is often unavailable. Moreover, these high-end devices are often disposed in fixed positions, and are difficult for the general patients to access.

In addition, with the development of data processing technology, more effective medical data algorithms continue to emerge. However, these algorithms require higher computation amount, and for a home portable medical device, it is difficult to run these algorithms on the home portable medical device. Currently, in order to calculate a large amount of complex medical data, one approach is to upload the data to a medical data center through the network for processing, and then download a result to a local end. But this approach may lead to a problem of privacy leakage of patient data. Another approach is to enhance the processing power of the local hardware. However, this approach is unrealistic for the grassroots medical clinics or in some remote areas. For a general medical device, enhancement of the local computing power will greatly increase the cost of the device, and frequency of using the enhanced local computing power in the whole life cycle of the device is not high, which will cause the waste of resources.

SUMMARY

A purpose of an embodiment of the present disclosure is to provide a medical data cluster processing system, a medical data cluster processing method, and a medical data processing method, so as to solve technical problems mentioned above.

According to at least an embodiment of the present disclosure, a medical data cluster processing system is provided. The medical data cluster processing system comprises: a cluster initiator device and cluster participant devices having signal connection with the cluster initiator. The cluster initiator device sends model data and medical data to at least two cluster participant devices; the cluster participant devices receive the model data and the medical data from the cluster initiator device, process the medical data based on the model data to obtain second processing data, and send the second processing data to the cluster initiator device; and the cluster initiator device receives the second processing data sent from the at least two cluster participant devices, and comprehensively processes the second processing data to obtain a medical data processing result.

For example, the cluster participant devices each comprise a safety processing virtual area, the safety processing virtual area is safely isolated from other areas of the cluster participant devices; and the cluster participant devices process the medical data based on the model data in the safety processing virtual area, so as to obtain the second processing data.

For example, the cluster initiator device accesses the safety processing virtual area of each cluster participant device and controls the processing in the safety processing virtual area, and the cluster participant devices do not have access to the safety processing virtual area.

According to at least an embodiment of the present disclosure, a medical data cluster processing method is provided, with a cluster comprising a cluster initiator device and at least two cluster participant devices, and the cluster initiator device and the at least two cluster participant devices having signal connection with each other. The medical data cluster processing method comprises: sending, by the cluster initiator device, model data and medical data to the at least two cluster participant devices respectively; receiving, by the cluster participant devices, the model data and the medical data from the cluster initiator device; processing, by the cluster participant devices, the medical data based on the model data received to obtain second processing data, and sending the second processing data to the cluster initiator device; and receiving, by the cluster initiator device, the second processing data sent from the at least two cluster participant devices, and comprehensively processing the second processing data to obtain a medical data processing result.

For example, the cluster initiator device divides the model data into multiple pieces of first sub data; the cluster initiator device sends a first sub data set including the multiple pieces of first sub data as a whole to each of the at least two cluster participant devices respectively; each cluster participant device receives the first sub data set from the cluster initiator device; and each cluster participant device processes the medical data based on the first sub data set received to obtain a corresponding piece of the second processing data, and sends the corresponding piece of the second processing data to the cluster initiator device.

For example, the cluster initiator device divides the model data into multiple pieces of first sub data, and divides the multiple pieces of first sub data into multiple groups; the cluster initiator device sends one or more groups of the first sub data to one of the at least two cluster participant devices, and sends other groups of the first sub data to others of the at least two cluster participant devices; each cluster participant device receives one or more groups of the first sub data from the cluster initiator device; and each cluster participant device processes the medical data based on the one or more groups of the first sub data received to obtain a corresponding piece of the second processing data, and sends the corresponding piece of the second processing data to the cluster initiator device.

For example, the medical data cluster processing method further comprises: dividing, by the cluster initiator device, the medical data into multiple pieces of second sub data; dividing, by the cluster initiator device, the multiple pieces of second sub data into at least two groups, assigning one or more groups of the second sub data to a second electronic device and assigning remaining groups of the second sub data to other second electronic devices; and processing, by each cluster participant device, one or more groups of the second sub data received based on the model data to obtain a corresponding piece of the second processing data, and sending corresponding piece of the second processing data to the cluster initiator device.

According to at least an embodiment of the disclosure, a medical data processing method, applied in a first electronic device, is provided. The medical data processing method comprises: sending model data and medical data to at least two second electronic devices, the second electronic devices being connected with the first electronic device; receiving multiple pieces of second processing data sent from the at least two second electronic devices, wherein the multiple pieces of second processing data are processing data obtained by processing the medical data based on the model data by the second electronic devices; and processing the multiple pieces of second processing data received from the at least two second electronic devices to obtain a medical data processing result.

For example, the model data comprises a first sub data set including multiple pieces of first sub data; and the first sub data set as a whole is sent to each of the at least two second electronic devices.

For example, the model data comprises a first sub data set including multiple pieces of first sub data; the multiple pieces of first sub data in the first sub data set are grouped to obtain a plurality of first sub data groups; at least one of the first sub data groups is sent to one of the at least two second electronic devices; and other first sub data groups are sent to others of the at least two second electronic devices.

For example, the medical data processing method comprises: obtaining processing performance parameters of the at least two second electronic devices; and sending the first sub data groups to the at least two second electronic devices based on the processing performance parameters of the at least two second electronic devices.

For example, at least two pieces of first sub data in the first sub data set are related to each other, and the at least two pieces of first sub data related to each other are sent to one second electronic device.

For example, at least two pieces of first sub data in the first sub data set are related to each other, and the at least two pieces of first sub data related to each other are respectively sent to different second electronic devices.

For example, the medical data processing method further comprises: receiving the second processing data sent from the at least two second electronic devices respectively; and correcting the second processing data to obtain third data.

For example, the medical data processing method comprises: determining an initial weight of each piece of first sub data; when a piece of first sub data in the first sub data set is sent to a second electronic device, sending an initial weight of the piece of first sub data to the second electronic device simultaneously; and based on initial weights of the multiple pieces of first sub data, processing the multiple pieces of second processing data received from the at least two second electronic devices to obtain third data.

For example, the medical data processing method comprises: receiving first processing data sent by the at least two second electronic devices, wherein the first processing data includes results obtained after the second electronic devices process the model data; and based on the first processing data, processing the multiple pieces of second processing data sent by the at least two second electronic devices to obtain third data.

For example, the model data comprises multiple pieces of first sub data, the first processing data comprises second weights of the multiple pieces of first sub data, the second weights are weights after processing the initial weights by the second electronic devices; the initial weights are the initial weights of the multiple pieces of first sub data sent to the second electronic devices; and the second processing data is processed based on the second weights of the multiple pieces of first sub data to obtain the third data.

For example, the medical data comprises a second sub data set including multiple pieces of second sub data; the multiple pieces of second sub data in the second sub data set are divided into at least two groups to obtain a plurality of second sub data groups; at least one of the second sub data groups is sent to one of the at least two second electronic devices; and other second sub data groups are sent to others of the at least two second electronic devices.

For example, the medical data processing method further comprises: after encrypting the model data and the medical data, sending the model data and the medical data to at least two second electronic devices, and receiving the encrypted second processing data sent by the at least two second electronic devices.

According to at least an embodiment of the disclosure, a medical data processing method, applied in at least two second electronic devices, comprising: receiving model data and medical data from a first electronic device, the second electronic devices being connected with the first electronic device; based on the model data, processing the medical data to obtain second processing data by the at least two second electronic devices respectively; and sending the second processing data to the first electronic device, so that the first electronic device processes the second processing data received from the at least two second electronic devices to obtain a medical data processing result.

For example, the model data comprises a first sub data set including multiple pieces of first sub data; the method comprises: receiving the first sub data set from the first electronic device; and based on the multiple pieces of first sub data in the first sub data set, processing the medical data to obtain the second processing data.

For example, the model data comprises a first sub data set including multiple pieces of first sub data, the multiple pieces of first sub data are divided into a plurality of first sub data groups; the method comprises: receiving at least one of the plurality of first sub data groups from the first electronic device; and processing the medical data based on the first sub data group to obtain the second processing data by the at least two second electronic devices.

For example, at least two groups of the first sub data groups in the first sub data set are related to each other; the method comprises: receiving the at least two groups of the first sub data groups related to each other from the first electronic device; and processing the medical data based on the at least two groups of the first sub data groups related to each other to obtain the second processing data by the at least two second electronic devices.

For example, the medical data processing method further comprises: receiving correction data of the second processing data sent from the first electronic device; and based on the correction data, obtaining an optimization parameter of the model data.

For example, the medical data processing method further comprises: receiving updated data of the second processing data sent from the first electronic device; and based on the correction data and the updated data, obtaining the optimization parameter of the model data.

For example, the medical data processing method further comprises: determining whether the model data needs to be changed or not; in a case that the model data needs to be changed, changing the model data to generate the first processing data; and sending the first processing data to the first electronic device, so that the first electronic device processes the second processing data based on the first processing data to obtain third data.

For example, the model data comprises multiple pieces of first sub data, the first processing data comprises second weights of the multiple pieces of first sub data, the second weights are weights obtained after the second electronic devices change initial weights; and the initial weights are initial weights of the multiple pieces of first sub data received from the first electronic device.

For example, the medical data comprises a second sub data set including multiple pieces of second sub data, the multiple pieces of second sub data in the second sub data set are divided into a plurality of second sub data groups, the method comprises: receiving at least one of the plurality of second sub data groups from the first electronic device; and based on the model data, processing the at least one of the plurality of second sub data groups to obtain the second processing data.

For example, each second electronic device comprises a safety processing virtual area, the safety processing virtual area is an area where the data is processed safely, the safety processing virtual area is safely isolated from other areas of the second electronic device, and the second electronic device stores the model data and the medical data in the safety processing virtual area, and processes the medical data based on the model data in the safety processing virtual area to obtain the second processing data.

For example, the second electronic device receives the encrypted model data and medical data from the first electronic device, encrypts the second processing data and sends the encrypted second processing data to the first electronic device.

BRIEF DESCRIPTION OF THE DRAWINGS

In order to clearly illustrate the technical solutions of the embodiments of the disclosure, the drawings of the embodiments will be briefly described in the following; it is obvious that the described drawings below only illustrate exemplary embodiments of the disclosure.

DETAILED DESCRIPTION

Figure 1:
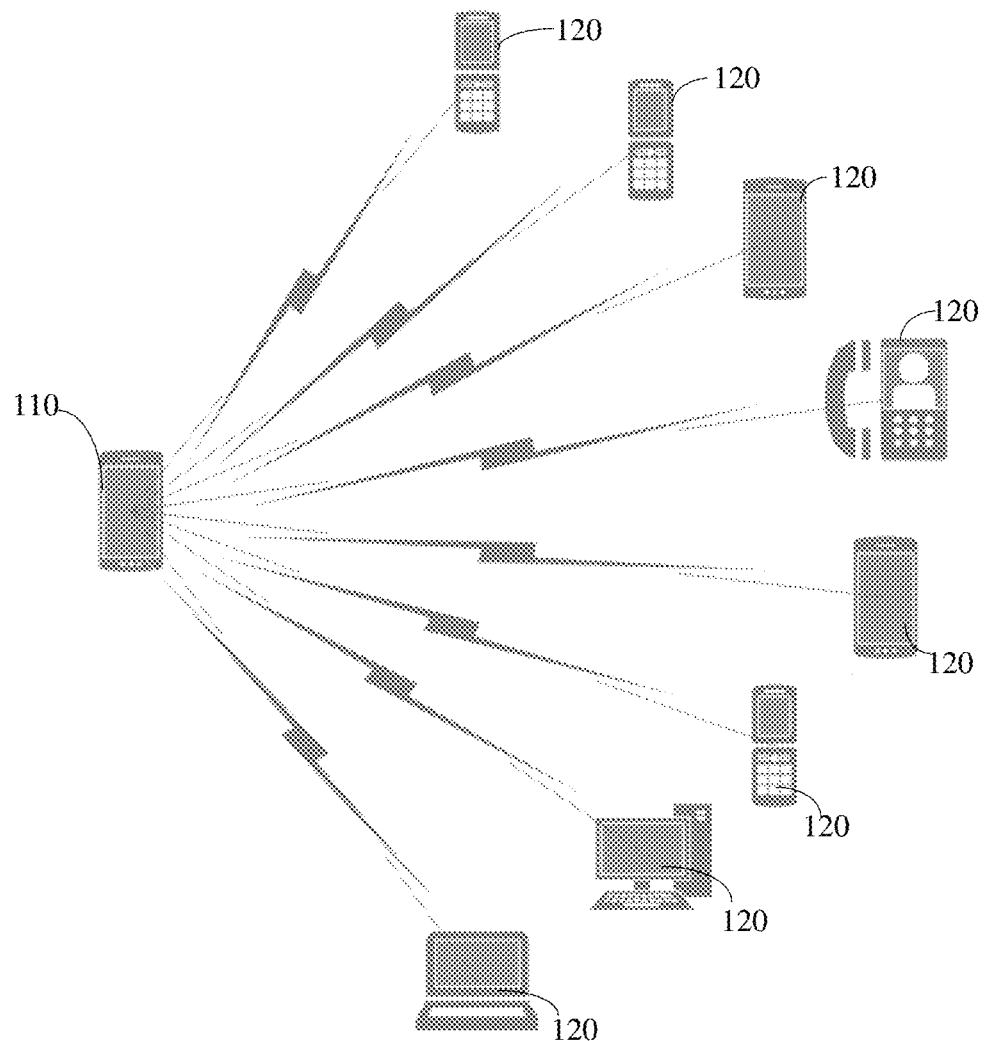
FIG. 1 shows an exemplary architecture diagram of a network model according to an embodiment of the present disclosure.

In the following, the preferred embodiments of the present disclosure will be described in detail with reference to the drawings. It should be noted that, in the specification and the drawings, a same label in the drawings represents to a basically identical step and element, and the repeated explanations of the identical steps and elements will be omitted.

In the following embodiments of the present disclosure, a first electronic device and a second electronic device are devices that are capable of communicating with other devices. Specific forms of the first electronic device and the second electronic comprise, but are not limited to, mobile terminals, personal computers, digital cameras, personal digital assistants, portable computers, etc. The electronic devices may also be terminal devices or server devices.

FIG. 1 shows an exemplary architecture diagram 100 of a network model according to an embodiment of the present disclosure. Referring to FIG. 1, in the network model of an embodiment of the present disclosure, a first electronic device 110, for example, is a device that initiates an electronic device cluster and controls the operation of the cluster, and the first electronic device 110 is referred to as an initiator device for convenience. A second electronic device 120, for example, is a device that responds to a broadcast message of the initiator device and participates in the cluster, and the second electronic device 120 is referred to as a participant device for convenience. In the network model, the network model may comprise only one first electronic device 110 and at least two second electronic devices 120. For example, in FIG. 1, the network model comprises eight second electronic devices 120. Based on the broadcast message of the initiator device, the initiator device and all of the participant devices may form a computer cluster at anytime and anywhere. The initiator device establishes and controls the cluster, the participant devices process medical data according to an instruction of the initiator device and communicates information with the initiator device. The structure and function of the initiator device and the participant devices are described respectively below.

Figure 2:
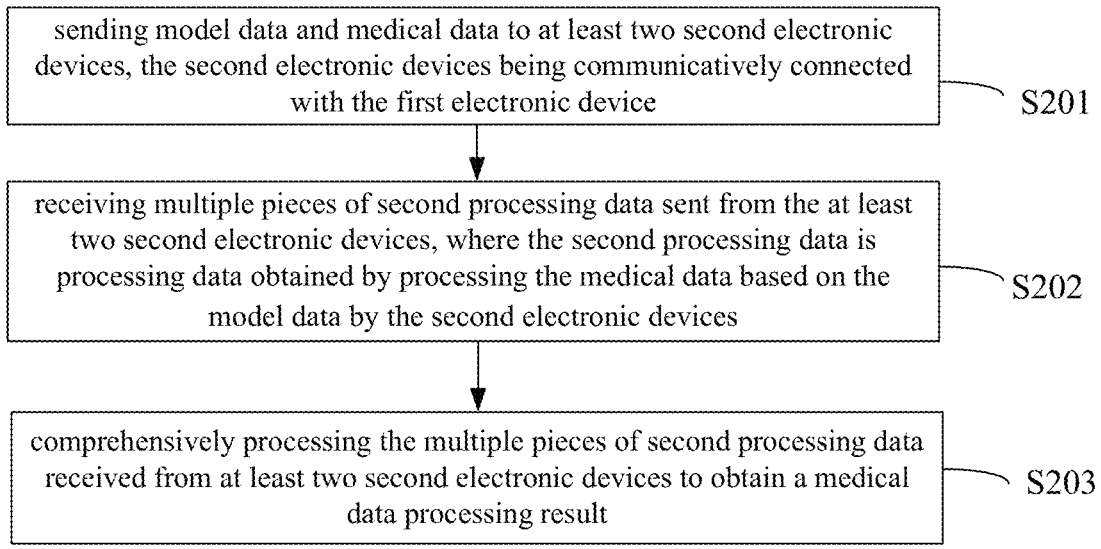
FIG. 2 shows an exemplary flow chart of a medical data acquisition method according to an embodiment of the present disclosure.

Firstly, a medical data acquisition method implemented by the initiator device is introduced. FIG. 2 shows an exemplary flow chart 200 of a medical data acquisition method according to an embodiment of the present disclosure, and the medical data acquisition method of an embodiment of the present disclosure will be described below with reference to FIG. 2.

Referring to FIG. 2, in the step S201: sending model data and medical data to at least two second electronic devices, the second electronic devices being communicatively connected with the first electronic device. For example, the model data may be processing model data used for processing the medical data, such as a processing algorithm, a processing model, a processing tool and the like. The model data may also be an analysis model random forest, and the random forest includes a plurality of irrelevant decision trees. The medical data may be medical data, such as a medical image, medical statistics data and the like. As described above, the first electronic device may be a cluster initiator device. The second electronic devices each may be a cluster participant device. The first electronic device and the second electronic devices may be communicated with each other through the network. In a case that the initiator device initiates a cluster establishment instruction through the network, after a participant device receives the cluster establishment instruction through the network, the participant device has a signal connection with the initiator device through the network, so as to participate in the cluster established by the initiator device. The cluster comprises the initiator device and at least two participant devices. Certainly, a person having ordinary skill in the art can understand that although in the present disclosure, a medical processing model processes the medical data, which is taken as an example to describe the medical data acquisition method, but the medical data acquisition method may also be applied to other technical fields. For example, an industrial processing model is used to process industrial data, a military processing model is used to process military data, etc.

After the cluster is established, the initiator device may send the model data and the medical data to at least two participant devices in the cluster. For example, in a case that a first electronic device needs to process complex medical data, the first electronic device may initiate a cluster establishment notification through the network, so as to request other electronic devices to process the medical data together. After two second electronic devices participate in the cluster, the first electronic device, as the initiator device, may send the medical data that needs to be processed and the processing model data of the medical data to respective second electronic devices respectively, so as to request respective second electronic devices to process the medical data together in parallel, and thus the processing ability and efficiency of the medical data is improved.

In the step S202: receiving multiple pieces of second processing data sent from the at least two second electronic devices. The second processing data is processing data obtained by processing the medical data based on the model data by the second electronic devices.

In a case that each second electronic device receives the model data and the medical data from the first electronic device, each second electronic device processes the medical data to obtain a corresponding piece of second processing data, and sends the piece of second processing data to the first electronic device. The first electronic device receives multiple pieces of second processing data. For example, a processing module used as the model data, analyzes a medical image used as the medical data. For example, a disease position in a pair or a piece of the medical images is analyzed and identified to obtain an analysis result. In order to ensure security of the data, the first electronic device may encrypt the model data and the medical data and then send the encrypted model data and medical data to at least two second electronic devices, and the first electronic device receives the corresponding second processing data encrypted and sent from respective second electronic devices.

In the step S203: comprehensively processing the multiple pieces of second processing data received from at least two second electronic devices to obtain a medical data processing result.

According to an embodiment of the present disclosure, the model data comprises a first sub data set including multiple pieces of first sub data. The initiator device respectively sends the first sub data set as a whole to each of the at least two second electronic devices. Each participant device processes the medical data based on all the first sub data in the first sub data set to obtain the corresponding second processing data, and sends the corresponding second processing data to the initiator device. For example, the processing model data used as the model data comprises a plurality of processing modules, each processing module acts as one first sub data, and all of the processing modules form the first sub data set. The initiator device may send the plurality of processing modules included in the processing model data to each participant device, each participant device processes the medical data according to the processing model data formed by the plurality of processing modules and sends the result to the initiator device. In this way, the initiator device may comprehensively process to obtain the medical data of the third data according to the processing data returned by each participant device. A comprehensive processing approach mentioned above, for example, may comprise performing statistical analysis on all data, determining a maximum, minimum or average value, and so on. For example, analysis results of each participant device on the disease are combined together to evaluate the disease comprehensively.

According to an embodiment of the present disclosure, the model data comprises a first sub data set including multiple pieces of first sub data. The initiator device may also send a part of the data in the first sub data set to one of the at least two second electronic devices, and send the other parts of the data in the first sub data set to the others of the at least two second electronic devices respectively. For example, the processing model data comprises a plurality of processing modules, each processing module acts as one piece of first sub data, and all processing modules form the first sub data set. Also for example, the model data is an analysis model random forest, with a plurality of irrelevant decision trees of the analysis model random forest being divided into a plurality of groups, and the plurality of groups is assigned to different participant devices. The initiator device may divide the plurality of processing modules included in the processing model data into multiple parts according to the number of the participant devices, and sends different parts to different initiator devices respectively. Each participant device processes the medical data according to the received one or more groups of processing modules or decision trees, and sends the result to the initiator device. In this way, in a case that the medical data is complex and the data processing model is also very large, the initiator may instruct each participant device to process the medical data according to a part of processing modules, and combine the processing results returned by each participant device to obtain a final medical data processing result. For example, the initiator device needs to analyze the medical data in different ways, and therefore the data processing model comprises a first analysis module, a second analysis module, . . . , and an Nth analysis module. In order to improve computing efficiency, the initiator device may divide the first analysis module, the second analysis module, . . . , and the Nth analysis module into several parts, and assign the several parts to a plurality of participant devices. The initiator device receives and combines the analysis results of respective participant devices, so as to improve the processing efficiency of the complex medical data.

According to an embodiment of the present disclosure, when the initiator device assigns the processing modules of the data processing model, the processing performance parameters of the participant device may be considered to set allocation rules. For example, the processing performance parameters can be obtained from the participant device, and based on the processing performance parameters of the participant device, the processing module(s) of the data processing model sent to the participant device is determined. For example, the initiator device obtains information of the participant devices, such as a processing speed of a processor, a storage capacity of a memory and so on, from the participant devices. The initiator device sends a processing module with a large amount of computation to a participant device with a high processing speed, and sends a processing module that generates a large amount of data to a participant device with a large storage capacity. By balancing the performance parameters of the participant devices, the advantages of each participant device may be utilized, so as to further improve the parallel processing capability of the cluster.

According to an embodiment of the present disclosure, in a case that part of the first sub data in the first sub data set is related to each other, for example, the first sub data and the second sub data are related to each other. The initiator device may send the first sub data and the second sub data which are related to each other to one second electronic device based on the relationship between the first sub data. For example, in a case that the data processing model comprises the first analysis module, the second analysis module and other processing modules; if the second analysis module is an analysis module based on an analysis result of the first analysis module, then the initiator device may send the first analysis module and the second analysis module to one participant device, and receive corresponding second processing data analyzed based on the first analysis module and the second analysis module from the participant device, so that a data transmission time between the initiator device and the plurality of participant devices is saved.

Certainly, the present disclosure is not limited thereto. According to another embodiment of the present disclosure, in a case that the first sub data and the second sub data in the first sub data set are related to each other, the initiator device may also send part of the first sub data related to each other to one second electronic device, and send the other part of the first sub data to other second electronic devices. For example, in a case that the data processing model comprises the first analysis module, the second analysis module and other processing modules; if the second analysis module is an analysis module based on an analysis result of the first analysis module, then the initiator device may also send the first analysis module to a participant device A and send the second analysis module to a participant device B. Under this circumstance, the participant device B may process the medical data by adopting other ways. For example, based on a first analysis result in previous historical data, the second analysis module may be used to analyze the first analysis result in the historical data to obtain an approximate analysis result. Or, based on the first analysis module in the historical data and the received second analysis module, the medical data is processed.

According to an embodiment of the present disclosure, the initiator device may also use the participant device to optimize the processing data model. After the participant device sends the processed second processing data to the initiator device, the initiator device may correct the second processing data and send correction data, e.g., the second processing data after being corrected, to the participant device again. The participant device obtains optimization parameters of the processing module(s) in the processing model data based on the received correction data.

In addition, according to an embodiment of the present disclosure, after the participant device sends the processed second processing data to the initiator device, in addition to correcting the second processing data, the initiator device may also update the data, such as adding new data, and send the corrected and updated data to the participant device again. The participant device obtains the optimization parameters of the processing module(s) in the processing model data based on the corrected and updated data being received.

In order to improve the parallelization of data processing, the initiator device may assign the processing modules with a processing sequence relationship in the processing data model to different participant devices, so that all participant devices may process the medical data in parallel compulsorily. In order to ensure the accuracy of the data, the initiator device may correct the processing result calculated by each participant device. The way in which the initiator device corrects the data, for example, may be a way in which the processing result is corrected by using known data, threshold data or an expected value.

According to an embodiment of the present disclosure, the initiator device may determine an initial weight of each first sub data in the first sub data set. When sending first sub data in the first sub data set to the participant device, the initial weight(s) of the corresponding first sub data is sent to the participant device simultaneously. In this way, when the second processing data received from at least two participant devices are combined, the initiator device may comprehensively process the multiple pieces of second processing data received from the at least two second electronic devices based on the initial weight(s) of the first sub data to obtain the third data. For example, in a case that the data processing model comprises a plurality of processing algorithms and each processing algorithm has a different initial weight based on the accuracy or effectiveness of the algorithm, the initiator device may obtain the final medical analysis result by multiplying the processing results received from the participant device by the corresponding weights.

According to an embodiment of the present disclosure, the participant device may process the processing model data sent by the initiator device, such as changing or correcting the processing model data. For example, after receiving the data processing model from the initiator device, the participant device determines whether the data processing model needs to be changed or not; in a case that the data processing model needs to be changed, the participant device changes the data processing model correspondingly. For example, in a case that the data processing model received from the initiator device comprises a plurality of processing modules and each processing module has an initial weight, under this circumstance, the participant device determines whether the initial weight of each received processing module needs to be changed or not according to the historical data thereof. In a case that the initial weight needs to be changed, the initial weight is modified to a second weight, and the second weight is returned to the initiator device subsequently. For example, in a case that the historical data shows that the initial weight received does not match with the corresponding processing module, it is determined that the initial weight needs to be changed, and then the participant device may change the initial weight correspondingly. The initiator device comprehensively evaluates the second processing data according to the second weight(s) to obtain the final medical analysis result. Certainly, the participant device changing the weight is just an example, and a person having ordinary skill in the art can understand that the participant device may also change other properties of the data processing model and the medical data received from the initiator device according to requirements. For example, the other properties comprise a version and content of the data processing model, a format and content of the medical data and so on.

According to an embodiment of the present disclosure, the medical data may comprise a second sub data set including multiple pieces of second sub data. The initiator device may send a first part of the second sub data in the second sub data set to one of the at least two second electronic devices, and send a second part of the second sub data in the second sub data set to the other(s) of the at least two second electronic devices respectively. For example, the medical data is a medical image, and the initiator device needs to recognize the medical image to determine whether the medical image has a lesion area. In order to improve the recognition efficiency, the initiator device may divide the medical image into a plurality of blocks, send one or more of the plurality of blocks to one participant device, and send the other blocks to other participant devices. Each participant device recognizes its received image block(s), and sends a recognition result to the initiator device. After the initiator device receives a corresponding recognition result of the recognized image block(s) sent from each participant device, the initiator device combines the recognition results to obtain the desired medical data. For example, after combining the recognition results, it can be determined whether the whole medical image has the lesion area, where the lesion area is located and so on. For example, each participant device scores each pixel in the image that is processed by itself to determine whether the pixel is the lesion area or not; after the initiator device receives the processing result, the initiator device may add the score of each participant device together to determine whether a sum of the scores exceeds to a preset threshold or not, so as to determine a location and size of the lesion area.

According to an example of the present disclosure, in order to ensure the safety of the medical data and protect the privacy of the patients, a safety processing virtual area may be disposed in part or all of the participant devices. The safety processing virtual area is safely isolated from the other areas of the participant device. The participant device stores the data processing model and the medical data received from the initiator device in the safety processing virtual area. And, the participant device processes the medical data based on the model data in the safety processing virtual area to obtain the second processing data. For example, the initiator device is provided with a sandbox mechanism; except that the initiator device may control the safety processing virtual area of the participant device and the processing operation in the safety processing virtual area, the other devices or components may not access and control the safety processing virtual area of the participant device. For example, even users of the participant device itself can not control the data processing in the safety processing virtual area, so as to ensure the closure of the whole process and the privacy of patient data. In addition, even if the data received from the initiator device contains a virus program, because all data received from the initiator device is stored in the safety processing virtual area and is processed isolatedly, other devices and components of the participant device are not affected by the virus program, and the safety of the participant device is ensured.

Through establishing a computer cluster, the present disclosure provides the feasibility of computing the complex medical data in parallel by existing general devices. Because the cluster may be established at anytime and anywhere, the flexibility of data processing is improved. Moreover, because the data is processed in the safety processing virtual area, so as to effectively protect the privacy of the patient data.

According to an embodiment of the present disclosure, a medical data processing method is provided, and the medical data processing method is applied to a participant device in a cluster, namely the medical data processing method is applied to a process that a cluster participant responses to an instruction of a cluster initiator to process the medical data. In the above description of operations performed by the initiator device in the cluster, operations performed by the cluster participant device has been described in details, and for the simplicity of the specification, a brief introduction will be given in the following, and the details may be referred to in the above embodiments.

Figure 3:
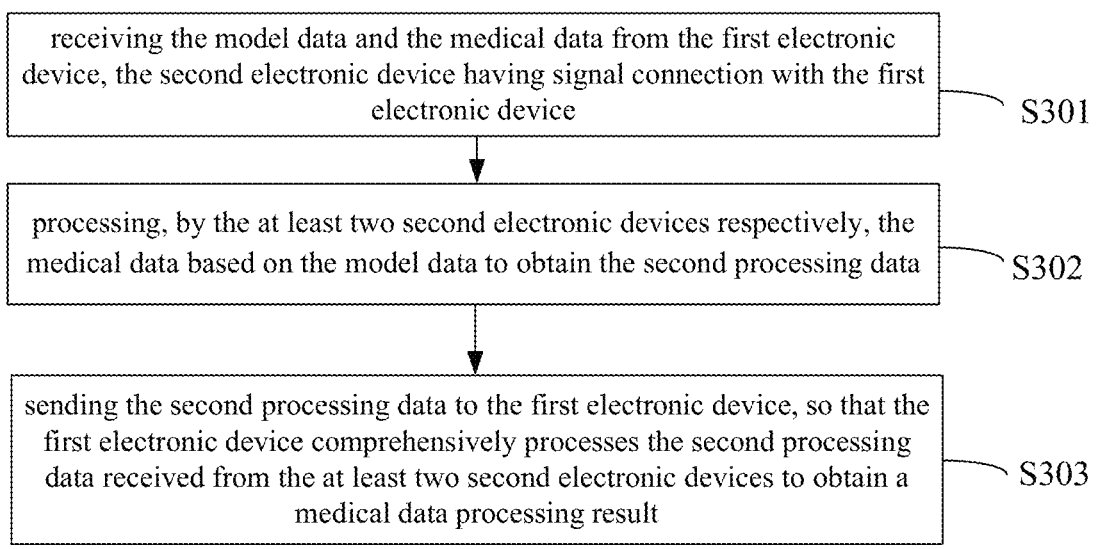
FIG. 3 shows an exemplary flow chart of a medical data processing method according to an embodiment of the present disclosure.

FIG. 3 shows an exemplary flow chart 300 of a medical data processing method according to an embodiment of the present disclosure. The medical data processing method is applied to at least two second electronic devices respectively. Referring to FIG. 3, in the step S301: receiving the model data and the medical data from the first electronic device, the second electronic device having signal connection with the first electronic device. In the step S302: processing, by the at least two second electronic devices respectively, the medical data based on the model data to obtain the second processing data. In the step S303: sending the second processing data to the first electronic device, so that the first electronic device comprehensively processes the second processing data received from the at least two second electronic devices to obtain a medical data processing result.

According to an example of the present disclosure, the model data comprises a first sub data set including multiple pieces of first sub data. The medical data processing method comprises: receiving the first sub data set from the first electronic device; and based on the multiple pieces of first sub data in the first sub data set, processing the medical data to obtain the second processing data.

According to an example of the present disclosure, the model data comprises a first sub data set including multiple pieces of first sub data, and the multiple pieces of first sub data are divided into a plurality of groups. The medical data processing method comprises: receiving one or more groups of the first sub data; and processing the medical data based on the one or more groups of the first sub data to obtain the second processing data.

According to an example of the present disclosure, at least two groups of the first sub data in the first sub data set are related to each other. The medical data processing method comprises: receiving two groups of the first sub data that are related to each other from the first electronic device; and processing the medical data based on the two groups of the first sub data related to each other to obtain the second processing data.

According to an example of the present disclosure, the medical data processing method comprises: receiving correction data of the second processing data sent from the first electronic device; and based on the correction data, obtaining an optimization parameter of the model data.

According to an example of the present disclosure, the medical data processing method comprises: receiving updated data of the second processing data sent from the first electronic device; and based on the correction data and the updated data, obtaining the optimization parameter of the model data.

According to an example of the present disclosure, the medical data processing method comprises: determining whether the model data needs to be changed or not; in a case that the model data needs to be changed, changing the model data to generate first processing data; and sending the first processing data to the first electronic device, so that the first electronic device processes the second processing data based on the first processing data to obtain the third data.

According to an example of the present disclosure, the model data comprises multiple pieces of first sub data, the first processing data comprises a second weight for each piece of the first sub data, and the second weight is a weight obtained after changing an initial weight by the second electronic device. The initial weight is the initial weight of a corresponding piece of the first sub data received from the first electronic device.

According to an example of the present disclosure, the medical data comprises a second sub data set including multiple pieces of second sub data, the multiple pieces of second sub data in the second sub data set are divided into at least two groups, and the medical data processing method comprises: receiving one or more groups of the second sub data from the first electronic device; and processing the one or more groups of the second sub data based on the model data to obtain the second processing data.

According to an example of the present disclosure, the second electronic device comprises a safety processing virtual area, the safety processing virtual area is safely isolated from the other areas of the second electronic device, and the second electronic device stores the model data and the medical data in the safety processing virtual area, and processes the medical data based on the model data in the safety processing virtual area to obtain the second processing data.

According to an example of the present disclosure, the second electronic device receives the encrypted model data and medical data from the first electronic device, encrypts the processed second processing data, and sends the encrypted second processing data to the first electronic device.

Embodiments of the present disclosure process the medical data in parallel, so as to improve the processing speed and the processing capacity. Moreover, because the cluster may be established at any time, so that the parallel computation of the complex medical data is possible without a large medical data processing device.

Figure 4:
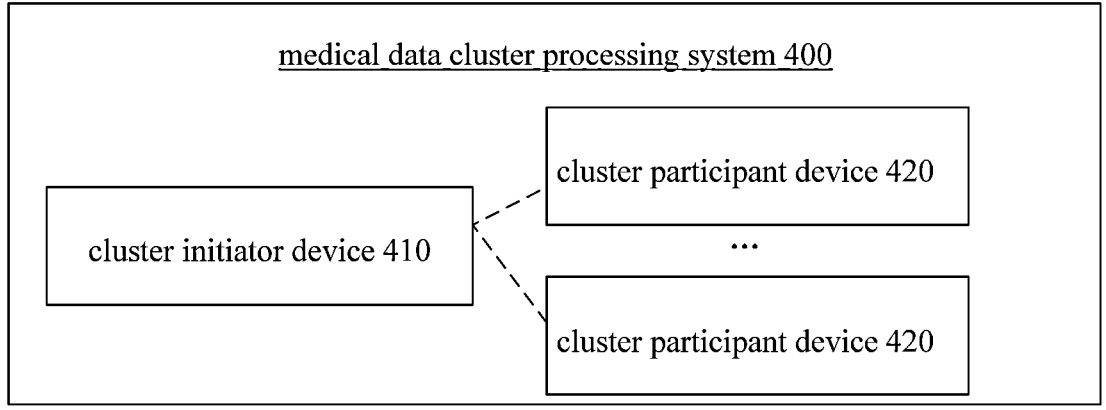
FIG. 4 shows an exemplary architecture diagram of a medical data cluster processing system according to an embodiment of the present disclosure.

According to an embodiment of the present disclosure, a medical data cluster processing system is provided. FIG. 4 shows an exemplary architecture diagram of a medical data cluster processing system according to an embodiment of the present disclosure. Referring to FIG. 4, the medical data cluster processing system 400 comprises a cluster initiator device 410 and cluster participant devices 420 as mentioned above. For the simplicity of the specification, a brief introduction will be given in the following, and the details may be referred to the above embodiments.

The cluster initiator device sends model data and medical data to at least two cluster participant devices; the cluster participant devices receive the model data and the medical data from the cluster initiator device, process the medical data based on the model data to obtain second processing data, and send the second processing data to the cluster initiator device; and the cluster initiator device receives the second processing data sent from the at least two cluster participant devices, and comprehensively processes the second processing data to obtain third data. The third data comprises medical data.

According to an example of the present disclosure, each cluster participant device comprises a safety processing virtual area, and the safety processing virtual area is safely isolated from the other areas of the cluster participant device; the cluster participant device processes the medical data based on the model data in the safety processing virtual area, so as to obtain the second processing data.

According to an example of the present disclosure, the cluster initiator device accesses the safety processing virtual area of the cluster participant device and controls the processing in the safety processing virtual area, and the cluster participant device is not capable of accessing the safety processing virtual area.

Embodiments of the present disclosure provide feasibility of computing the complex medical data through establishing the computer cluster. Moreover, because the data is processed in the safety processing virtual areas, so as to effectively protect the privacy of the patient data.

According to an embodiment of the present disclosure, a medical data cluster processing method is provided. The medical data cluster processing method corresponds to the cluster processing system in the embodiments mentioned above, the cluster initiator device and the cluster participant devices in the medical data cluster processing method are similar to the cluster initiator device and the cluster participant devices in the embodiments described above. For the simplicity of the specification, a brief introduction will be given in the following, and the details may be referred to the description in the above embodiments.

Figure 5:
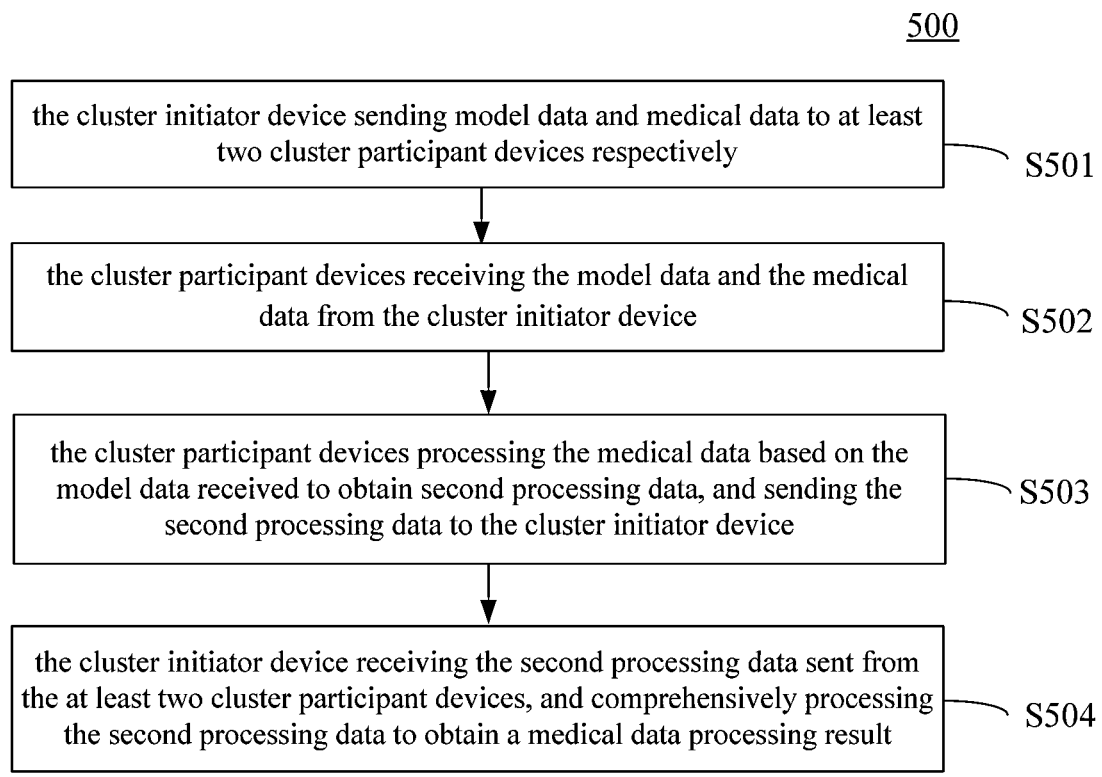
FIG. 5 shows a flow chart of a medical data cluster processing method according to an embodiment of the present disclosure.

In the medical data cluster processing method, the cluster comprises a cluster initiator device and at least two cluster participant devices, and the cluster initiator device has signal connection with the at least two cluster participant devices. FIG. 5 shows a flow chart 500 of a medical data cluster processing method according to an embodiment of the present disclosure. Referring to FIG. 5, in the step S501: the cluster initiator device sending model data and medical data to at least two cluster participant devices respectively. In the step 502: the cluster participant devices receiving the model data and the medical data from the cluster initiator device. In the step S503: the cluster participant devices processing the medical data based on the model data received to obtain second processing data, and sending the second processing data to the cluster initiator device. In the step S504: the cluster initiator device receiving the second processing data sent from the at least two cluster participant devices, and comprehensively processing the second processing data to obtain a medical data processing result.

According to an example of the present disclosure, the cluster initiator device divides the model data into multiple pieces of first sub data, the cluster initiator device sends a first sub data set including the multiple pieces of first sub data as a whole to each of the at least two cluster participant devices; each cluster participant device receives the first sub data set from the cluster initiator device; and each cluster participant device processes the medical data based on the first sub data set received to obtain a corresponding piece of second processing data, and sends the corresponding piece of second processing data to the cluster initiator device.

According to an example of the present disclosure, the cluster initiator device divides the model data into multiple pieces of first sub data, and divides the multiple pieces of first sub data into a plurality of groups; the cluster initiator device sends one or more groups of the first sub data to one of the at least two cluster participant devices, and sends other groups of the first sub data to the others of the at least two cluster participant devices; each cluster participant device receives one or more groups of the first sub data from the cluster initiator device; each cluster participant device processes the medical data based on the one or more groups of the first sub data received to obtain a corresponding piece of the second processing data, and sends the corresponding piece of the second processing data to the cluster initiator device.

According to an example of the present disclosure, the cluster initiator device divides the medical data into multiple pieces of second sub data, the cluster initiator device divides the multiple pieces of second sub data into at least two groups, the cluster initiator device assigns one or more groups of the second sub data to a second electronic device and assigns the other groups of the second sub data to the other second electronic devices; each cluster participant device processes one or more groups of the second sub data received based on the model data to obtain the corresponding piece of the second processing data, and sends the corresponding piece of the second processing data to the cluster initiator device.

Embodiments of the present disclosure adopt the computer cluster to process the medical data, so that the complex medical data may be calculated and processed rapidly.

A person having ordinary skill in the art can realized that, in combination with the embodiments of the present disclosure described in the specification, units and algorithm steps of each example can be implemented by electronic hardware, computer software or the combination of the two. In addition, each software module may be stored in computer storage media having any form. In order to clearly describe interchangeability of hardware and software, in the above description, components and steps of each example have been described in general according to functions. The functions are implemented in hardware or in software, which depends on the particular application and design constraints of the technical solution. A person having ordinary skill in the art may use different methods to implement the described function for each particular application, but the implementation of the described function should not be understood as being outside the scope of the disclosure.

A person having ordinary skill in the art should understand that various modification, combinations, partial combinations and substitutions may be made to the present disclosure depending on design requirement and other factors, provided that all of the modification, combinations, partial combinations and substitutions fall within the scope of the claims and equivalents thereof.

The application claims priority to the Chinese patent application No. 201610810601.8, filed Sep. 8, 2016, the entire disclosure of which is incorporated herein by reference as part of the present application.

What is claimed is:

1. A medical data cluster processing method, with a cluster comprising a cluster initiator device and at least two cluster participant devices, and the cluster initiator device and the at least two cluster participant devices having signal connection with each other, comprising:
    initiating, by the cluster initiator device in a case where the cluster initiator device processes data medical image, a cluster establishment notification to request the at least two cluster participant devices to participate a cluster to process the medical image together with the cluster initiator device;
    receiving, by the at least two cluster participant devices, the cluster establishment notification and participating the cluster in response to the cluster establishment notification;
    sending, by the cluster initiator device, model data and the medical image to each of the at least two cluster participant devices respectively;
    receiving, by each of the at least two cluster participant devices, the model data and the medical image from the cluster initiator device;
    performing, by each of the at least two cluster participant devices, an image recognition operation on the medical image based on the model data received to obtain a recognition result, and sending the recognition result to the cluster initiator device;
    receiving, by the cluster initiator device, the recognition results sent from the at least two cluster participant devices, and comprehensively processing the recognition results to determine a location and a size of a lesion area in the medical image,
    wherein the image recognition operation comprises determining a score of each pixel in an area of the medical image which is processed by the cluster participant device and using the score as the recognition result; and
    the comprehensively processing the recognition results to determine the location and the size of the lesion area in the medical image comprises adding the scores sent from the at least two cluster participant devices to determine whether a sum of the scores exceeds a preset threshold, and determining the location and the size of the lesion area in the medical image in a case that it is determined that the sum of the scores exceeds the preset threshold.

2. The medical data cluster processing method according to claim 1, wherein:
    the cluster initiator device divides the model data into multiple pieces of first sub data;
    the cluster initiator device sends a first sub data set comprising the multiple pieces of first sub data as a whole to each of the at least two cluster participant devices respectively;
    each of the at least two cluster participant devices receives the first sub data set from the cluster initiator device; and
    each of the at least two cluster participant devices performs the image recognition operation on the medical image based on the first sub data set received to obtain a corresponding recognition result, and sends the corresponding recognition result to the cluster initiator device.

3. The medical data cluster processing method according to claim 1, wherein:
    the cluster initiator device divides the model data into multiple pieces of first sub data, and divides the multiple pieces of first sub data into multiple groups;
    the cluster initiator device sends one or more groups of the first sub data to one of the at least two cluster participant devices, and sends other groups of the first sub data to others of the at least two cluster participant devices;
    each of the at least two cluster participant devices receives one or more corresponding groups of the first sub data from the cluster initiator device; and
    each of the at least two cluster participant devices performs the image recognition operation on the medical image based on the one or more groups of the first sub data received to obtain a corresponding recognition result, and sends the corresponding recognition result to the cluster initiator device.

4. The medical data cluster processing method according to claim 3, further comprising:
    obtaining, by the cluster initiator device, processing performance parameters of the at least two cluster participant devices; and
    sending, by the cluster initiator device, the multiple groups to the at least two cluster participant devices based on the processing performance parameters of the at least two cluster participant devices.

5. The medical data cluster processing method according to claim 3, wherein at least two pieces of first sub data are related to each other, and the at least two pieces of first sub data related to each other are sent to one cluster participant device.

6. The medical data cluster processing method according to claim 3, wherein at least two pieces of first sub data are related to each other, and the at least two pieces of first sub data related to each other are respectively sent to different cluster participant devices.

7. The medical data cluster processing method according to claim 6, further comprising:
receiving, by the cluster initiator device, the recognition results sent from the at least two cluster participant devices respectively; and
correcting, by the cluster initiator device, the recognition results to determine the location and the size of the lesion area in the medical image.

8. The medical data cluster processing method according to claim 3, wherein at least two groups of the multiple groups are related to each other, and the method further comprises:
receiving, by the at least two cluster participant devices, the at least two groups of the multiple groups related to each other from the cluster initiator device; and
performing, by the at least two cluster participant devices, the image recognition operation on the medical image based on the at least two groups of the multiple groups related to each other to obtain the recognition results.

9. The medical data cluster processing method according to claim 1, further comprising:
receiving, by the cluster initiator device, first processing data sent by the at least two cluster participant devices, wherein the first processing data comprises results obtained after the cluster participant devices process the model data; and
based on the first processing data, processing, by the cluster initiator device, the recognition results sent by the at least two cluster participant devices to determine the location and the size of the lesion area in the medical image.

10. The medical data cluster processing method according to claim 9, wherein the model data comprises multiple pieces of first sub data;
the first processing data comprises second weights of the multiple pieces of first sub data, the second weights are weights after processing the initial weights by the cluster participant devices;
the initial weights are the initial weights of the multiple pieces of first sub data sent to the cluster participant devices; and
the recognition result is processed based on the second weights of the multiple pieces of first sub data to determine the location and the size of the lesion area in the medical image.

11. The medical data cluster processing method according to claim 1, further comprising:
determining, by the at least two cluster participant devices, whether the model data needs to be changed or not;
changing, by the at least two cluster participant devices, the model data to generate first processing data in a case that it is determined that the model data needs to be changed; and
sending, by the at least two cluster participant devices, the first processing data to the cluster initiator device, so that the cluster initiator device processes the recognition results based on the first processing data to determine the location and the size of the lesion area in the medical image.

12. The medical data cluster processing method according to claim 11, wherein the model data comprises multiple pieces of first sub data,
the first processing data comprises second weights of the multiple pieces of first sub data, the second weights are weights obtained after the at least two cluster participant devices change initial weights, and the initial weights are initial weights of the multiple pieces of first sub data received from the cluster initiator device.

13. The medical data cluster processing method according to claim 1, wherein the medical image comprises a block set comprising multiple blocks of the medical image;
the multiple blocks of the medical image in the block set are divided into at least two groups to obtain a plurality of block groups;
at least one of the block groups is sent to one of the at least two cluster participant devices; and
other block groups are sent to others of the at least two cluster participant devices.

14. The medical data cluster processing method according to claim 13, further comprising:
receiving, by the at least two cluster participant devices, the at least one of the block groups from the cluster initiator device; and
based on the model data, performing, by the at least two cluster participant devices, the image recognition operation on the at least one of the block groups to obtain the recognition result.

15. The medical data cluster processing method according to claim 13, further comprising:
dividing, by the cluster initiator device, the medical image into the multiple blocks;
dividing, by the cluster initiator device, the multiple blocks into the at least two groups, assigning one or more block groups to a cluster participant device, and assigning remaining block groups to other cluster participant devices; and
performing, by each of the at least two cluster participant devices, the image recognition operation on a received block group based on the model data to obtain a corresponding recognition result, and sending the corresponding recognition result to the cluster initiator device.

16. The medical data cluster processing method according to claim 1, further comprising:
receiving, by the at least two cluster participant devices, correction data of the recognition results sent from the cluster initiator device; and
based on the correction data, obtaining, by the at least two cluster participant devices, an optimization parameter of the model data.

17. The medical data cluster processing method according to claim 16, further comprising:
receiving, by the at least two cluster participant devices, updated data of the recognition results sent from the cluster initiator device; and
based on the correction data and the updated data, obtaining, by the at least two cluster participant devices, the optimization parameter of the model data.

18. The medical data cluster processing method according to claim 1, further comprising:
encrypting, by the cluster initiator device, the model data and the medical image, and sending the encrypted model data and medical image to the at least two cluster participant devices;
receiving, by each of the at least two cluster participant devices, the encrypted model data and medical image from the cluster initiator device, encrypting the recognition result, and sending the encrypted recognition result to the cluster initiator device; and receiving, by the cluster initiator device, the encrypted recognition result sent by the at least two cluster participant devices.

19. The medical data cluster processing method according to claim 1, wherein each of the at least two cluster participant devices comprises a safety processing virtual area, the safety processing virtual area is safely isolated from other areas of the cluster participant devices; and each of the at least two cluster participant devices performs the image recognition operation on the medical image based on the model data in the safety processing virtual area, so as to obtain the recognition result.

20. The medical data cluster processing method according to claim 19, wherein the cluster initiator device accesses the safety processing virtual area of each cluster participant device and controls the processing in the safety processing virtual area, and the cluster participant devices do not have access to the safety processing virtual area.

* * * * *